United States Patent
Miyazaki et al.

(10) Patent No.: US 7,817,828 B2
(45) Date of Patent: Oct. 19, 2010

(54) IMAGE PROCESSOR FOR MEDICAL TREATMENT SUPPORT

(75) Inventors: Osamu Miyazaki, Ibaraki (JP); Hiromitsu Hayashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 869 days.

(21) Appl. No.: 10/576,595

(22) PCT Filed: Oct. 22, 2004

(86) PCT No.: PCT/JP2004/015692
§ 371 (c)(1),
(2), (4) Date: Apr. 2, 2007

(87) PCT Pub. No.: WO2005/039416
PCT Pub. Date: May 6, 2005

(65) Prior Publication Data
US 2008/0027314 A1    Jan. 31, 2008

(30) Foreign Application Priority Data
Oct. 23, 2003  (JP)  ............................. 2003-363921

(51) Int. Cl.
*G06K 9/00* (2006.01)
*A61B 5/05* (2006.01)

(52) U.S. Cl. ...................................... 382/128; 600/425
(58) Field of Classification Search ................. 382/128, 382/129, 130, 131, 132, 133, 134; 378/4, 378/21, 22, 23, 24, 25, 26, 27, 28, 62, 901; 600/407, 410, 411, 425, 427, 429; 128/920, 128/922
See application file for complete search history.

(56) References Cited

U.S. PATENT DOCUMENTS

| 5,553,618 A | * | 9/1996 | Suzuki et al. | ............... 600/411 |
| 5,590,653 A | * | 1/1997 | Aida et al. | .................. 600/411 |
| 6,760,402 B2 | * | 7/2004 | Ghelmansarai | .............. 378/65 |

FOREIGN PATENT DOCUMENTS

| JP | 2000-300591 | 10/2000 |
| JP | 2003-10228 | 1/2003 |

* cited by examiner

Primary Examiner—Abolfazl Tabatabai
(74) Attorney, Agent, or Firm—Cooper & Dunham LLP

(57) ABSTRACT

An image for treatment region considered as already completed treatment in the course of medical treatment is acquired. Time up to completion of the whole scope of intended treatment regions is estimated on the basis of the already completed treatment region.

16 Claims, 11 Drawing Sheets

(A)

(B)

IMAGE PROCESSOR FOR MEDICAL TREATMENT SUPPORT

BACKGROUND ART

The present invention relates to an image processor for medical treatment support by which improvement in planning and efficacy can be achieved by monitoring an image of a target area upon treatment of the target area of an object to be examined.

TECHNICAL FIELD

The apparatuses such as X-ray CT or MRI are commonly known to be useful for image diagnosis, and are also widely applied as a guide for monitoring treatment of surgical operations or biopsy, not only as a mere diagnostic device for displaying images. The objective of using these apparatuses in the case of a biopsy is to figure out the positional relations between a puncture needle and a lesion, and the means in use are such as CT/MR fluoroscopy that enables grasping the positional relations in real time by contriving the reconstruction process and sequentially renewing the image. As for treatment, availability of various means and methods such as hyperthermia using a laser, RF (Radio Frequency) or cryo-surgery using gas are under consideration. Also for a modality to use for monitoring, attempts are being made to use various types of image diagnostic apparatuses such as CT, MRI or US, each of which has its advantages and disadvantages. Descriptions relating to these methods of monitoring treatment are found in the following Patent Documents 1~3.

Patent Document 1: JP-A-2003-10228
Patent Document 2: JP-A-2000-300591
Patent Document 3: JP-A-2003-88508

DISCLOSURE OF THE INVENTION

The Problems

For example, treatment for disk herniation using a laser is performed by irradiating an interspinal disk with a laser and evaporating the moisture in the interspinal disk, by which the compression on the nerves caused by the herniation is reduced. CT apparatus can contribute in estimating the condition of the evaporation if the degree of the gas evaporation is acquired. Also for example, for treatment of diseases such as a tumor, a method of necrotization of the tissues of the tumor by heating or freezing the lesion is carried out. Cryosurgery being one example of the above method, takes a means to carry out the treatment to check if the lesion is covered sufficiently by the frozen region (Ice Ball).

MRI apparatus being high in tissue contrast is often used for monitoring, rather than ultrasound (US) apparatus that is not capable of observing the shadow of the ice ball. CT apparatus can also be used for monitoring. However, there are problems related to monitoring these complicated procedures as images need to be acquired sequentially during treatment, additionally in the case of using X-ray CT apparatus, that the dose of radiation exposure on the patient increases with the number of images acquired. Also, even though the region being treated needs to be somewhat larger than the lesion, there is a demand to reserve the normal tissues as much as possible, thus the need to depend on visual observation for determining the region for treatment is unavoidable at this point. However, it has been difficult to visually distinguish a freezing region from the lesion border as the treatment. Further, even though there is basic data in what degree of temperature is pathologically necessary for necrotization of tissues, it has been difficult to carry out reliable treatment procedure since there was no means to measure it quantitatively and check the relationship between the lesion and the temperature distribution.

The above-mentioned issues are taken into consideration by the present invention, and the objective of the invention is to provide an image processor for medical treatment support by which the time required to complete a treatment upon monitoring of the treatment can be estimated.

The present invention is also to provide an image processor for medical treatment support by which a lesion and the range of temperature for an effective treatment can be easily acquired upon monitoring of treatment, taking the above-mentioned issues into consideration.

Means for Solving Problems

The present invention provides an image processor for medical treatment support that obtains a tomographic image of the object to be examined, and monitors the treatment process, comprising:
  a treatment target region setting means for selecting a monitoring image from the tomographic image, and setting the treatment target region on the selected image;
  a treatment-completed region setting means for setting on the monitoring image the region being considered where the treatment has already been completed; and
  a total treatment time estimating means for estimating the time for completing the treatment of the treatment target region being set by the treatment target region setting means, based on the treatment-completed region.

Also, the total treatment time estimating means is for obtaining each of the distances from the reference point that is the starting point of the treatment to the border of the treatment-completed region with regard to the treatment-completed regions on a plurality of the monitoring images, and estimating the total treatment time based on the change of those distances.

Also, the total treatment time estimating means is for setting the straight lines extended radially with equiangular intervals from the reference point of the treatment target region as the reference lines, and estimating the total treatment time based on the degree of treatment progress on the reference lines.

Also, the total treatment time estimating means is for specifying at least one reference line that bisects the treatment target region from the reference point, obtaining the points of which a perpendicular line that divides the reference line into predetermined intervals intersects with the treatment target region, setting the lines that connect those points and the reference point as further reference lines, and estimating the total treatment time according to the degree of treatment progress on those reference lines.

Also, the total treatment time estimating means is for setting the lines that connect the pixels of predetermined intervals on the display means for displaying the outline of the treatment target region and the reference point as the reference lines, and estimating the total treatment time according to the degree of treatment progress on the reference lines.

Also, the treatment target region setting means is for setting a plurality of closed curves by synthesizing them and smoothing their crossed portion, and the total treatment time estimating means is for setting the reference line on every closed curve and estimating the total treatment time according to the degree of treatment progress on those plurality of reference lines.

The present invention provides an image processor for medical treatment support that obtains a tomographic image of an object to be examined and monitors treatment progress comprising:

a treatment target region setting means for selecting a monitoring image from the tomographic image, and setting a target treatment region on the monitoring image;

a treatment-completed region setting means for setting on the monitoring image a region being considered on which treatment has already been completed; and a display means for estimating a treatment region after the passing of a predetermined period of time according to the treatment-completed region, and displaying this estimated treatment region with at least one hue information.

Also, the display means is for displaying the treatment target region, the treatment-completed region and the estimated treatment region by allocating different hue information to each region.

Also, the display means is for displaying by allocating hue information on the treatment target region.

Also, the display means is for displaying the shifting of the region under treatment with color, as well as displaying by allocating the hue information on the treatment target region.

Also, the display means is for displaying by allocating different hue information to the treatment-completed regions at a plurality of time points.

Also, the display means is for displaying by allocating hue information to the estimated treatment-completed regions in incremental steps.

Also, the display means is for displaying the estimated treatment regions at a plurality of time points with desired color gradation.

Also, the display means is for displaying by superimposing one or both, the estimated treatment region, and the treatment-completed region with the treatment target region.

The present invention provides an image processor for medical treatment support that obtains a tomographic image of an object to be examined, and monitors the treatment progress, comprising;

an image memory for storing data for creating a tomograpphic image;

a measurement calculating means for calculating measurement value from the data for creating the tomograpphic image;

a measurement/temperature converting means for converting measurement value into a temperature;

a color table for allocating the hue information to the converted temperature and displaying the temperature with colors;

a look-up table for allocating the gray scale to the data for creating the tomographic image being stored in the image memory;

a monitoring mode switch for prompting synthesis of color display of the temperature and data for creating a tomographic image being allocated with gray scale; and a display means for displaying the synthesized color display of the temperature and the data for creating the tomographic image as an image.

Also, the measurement/temperature converting means is for setting a CT value as a measurement value, and converting CT value into a temperature by assuming the tissue of which the CT value of the vicinity of 25-degrees is 0 has −20 to −50 of CT value in below 0-degree.

Further, it also comprises:

a treatment support display mode selecting means for selecting the display mode for medical treatment support;

a time selecting and input means for inputting the time of starting the treatment for the desired treatment progress image to be displayed;

a treatment progress image creating means for creating the treatment progress image of the selected time; and a display means for displaying the treatment progress image and one or both of the treatment target region and/or the treatment-completed region.

It also comprises a difference image creating means for creating the difference image between the treatment progress image and one or both of the treatment target region and/or treatment-completed region, and the display means is for displaying the difference image and one or both of treatment target region and/or treatment-completed region.

Also, the display means is for displaying the treatment target region, the treatment-completed region, the treatment progress image and the difference image by allocating different hue information to each of them.

Advantageous Effect of the Invention

According to the present invention, by estimating the time needed for completing the treatment upon monitoring it, it is possible to improve remaining treatment planning and to reduce the number of images that must be obtained. Also, the lesion and the region of the temperature effective for the treatment can be easily calculated.

BEST MODE FOR CARRYING OUT THE INVENTION

Embodiment 1

Hereinafter embodiment 1 of the present invention will be described referring to the attached drawings.

Figure 1:
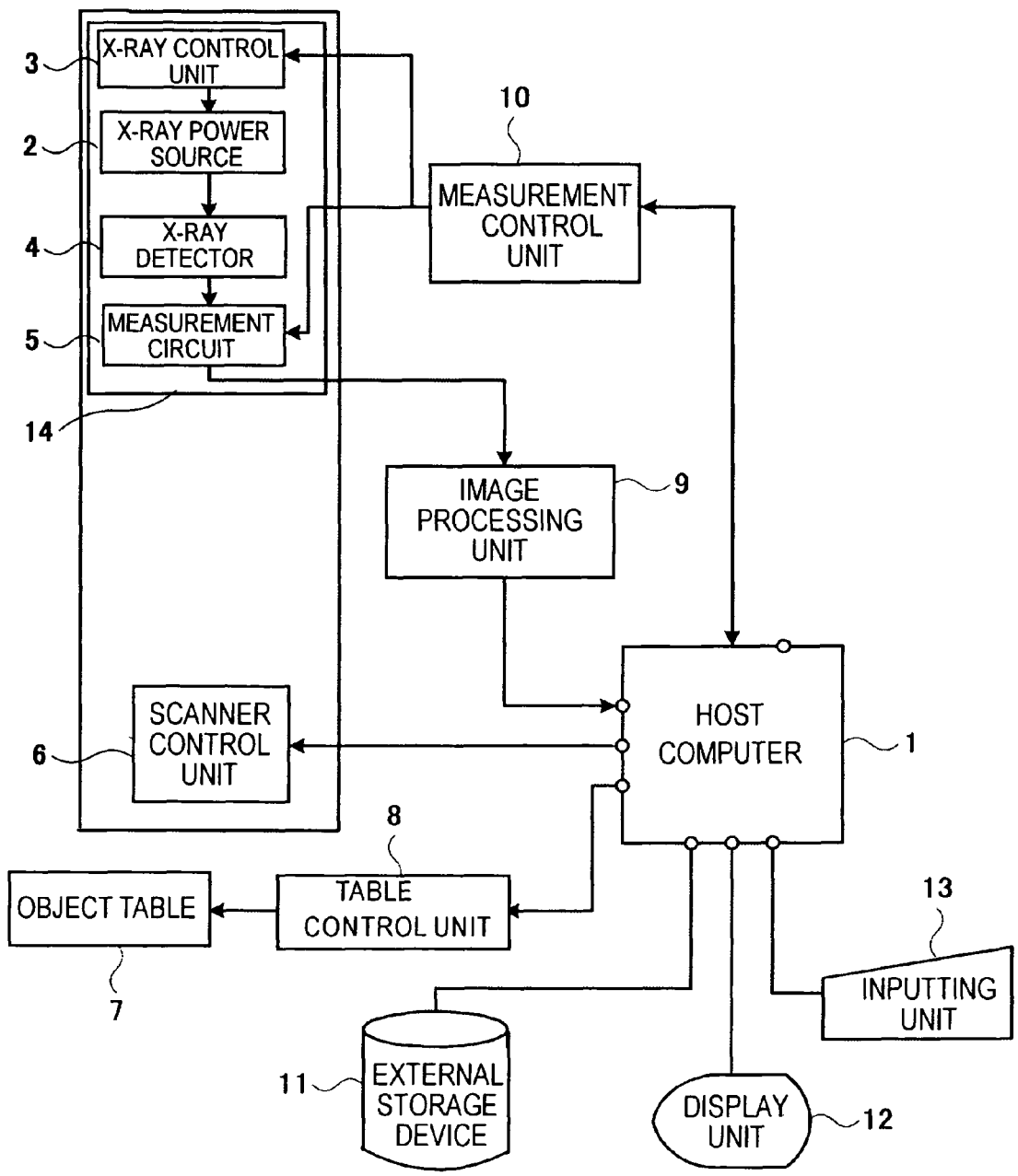
FIG. 1 is a block diagram showing an embodiment of an image processor for medical treatment support by the present invention.

FIG. 1 is a block diagram showing an embodiment of an image processor for medical treatment support by the present invention. This image processor for medical treatment support comprises:

host computer 1 for overall controlling of the entire system;
turntable 14 being mounted with the measurement units such as X-ray power source 2, X-ray controlling unit 3, X-ray detector 4 and measurement circuit 5;
scanner controlling unit 6 for controlling the rotating scan of turntable 14;
transportable object table 7 and table controlling unit 8 for determining the position of an object to be examined or for the helical scanning; and
image processor 9 for executing various types of image processing such as pre-processing or reconstructive processing. Measurement controlling unit 10 is for controlling the operation of X-ray controlling unit 3 and measurement circuit 5 being mounted in turntable 14 of the scanner, according to the instruction from host computer 1. X-ray controlling unit 3 and measurement circuit 5 are for starting up a measurement operation of X-ray radiation and data measurement according to the instruction from measurement controlling unit 10. External storage device 11 is a device such as a magnetic disk, a floppy disk drive, a hard disk drive, a CD-ROM drive, a magnetic optical disk (MO) drive, a ZIP drive, a PD drive, and a DVD drive for storing a controlling program for the entire device, or for storing measurement data being outputted from measurement circuit 5, tomographic data being obtained by processing the measurement data or various types of programs. Display device 12 is a device such as display memory for storing image data temporarily, and CRT display for displaying an image based on the image data from the display memory. Inputting device 13 comprises a mouse for operating a soft switch on the screen, a controller of the mouse, and a keyboard including a key or switch for setting various types of parameter, and is for inputting various types of commands and information to host computer 1. Host computer 1 can make the image processor for medical treatment support of such configuration connectable via communication interface to all sorts of communication networks such as LAN (local area network), Internet, and phone line, and to be able to exchange the image data with other computers or CT devices.

Figure 2:
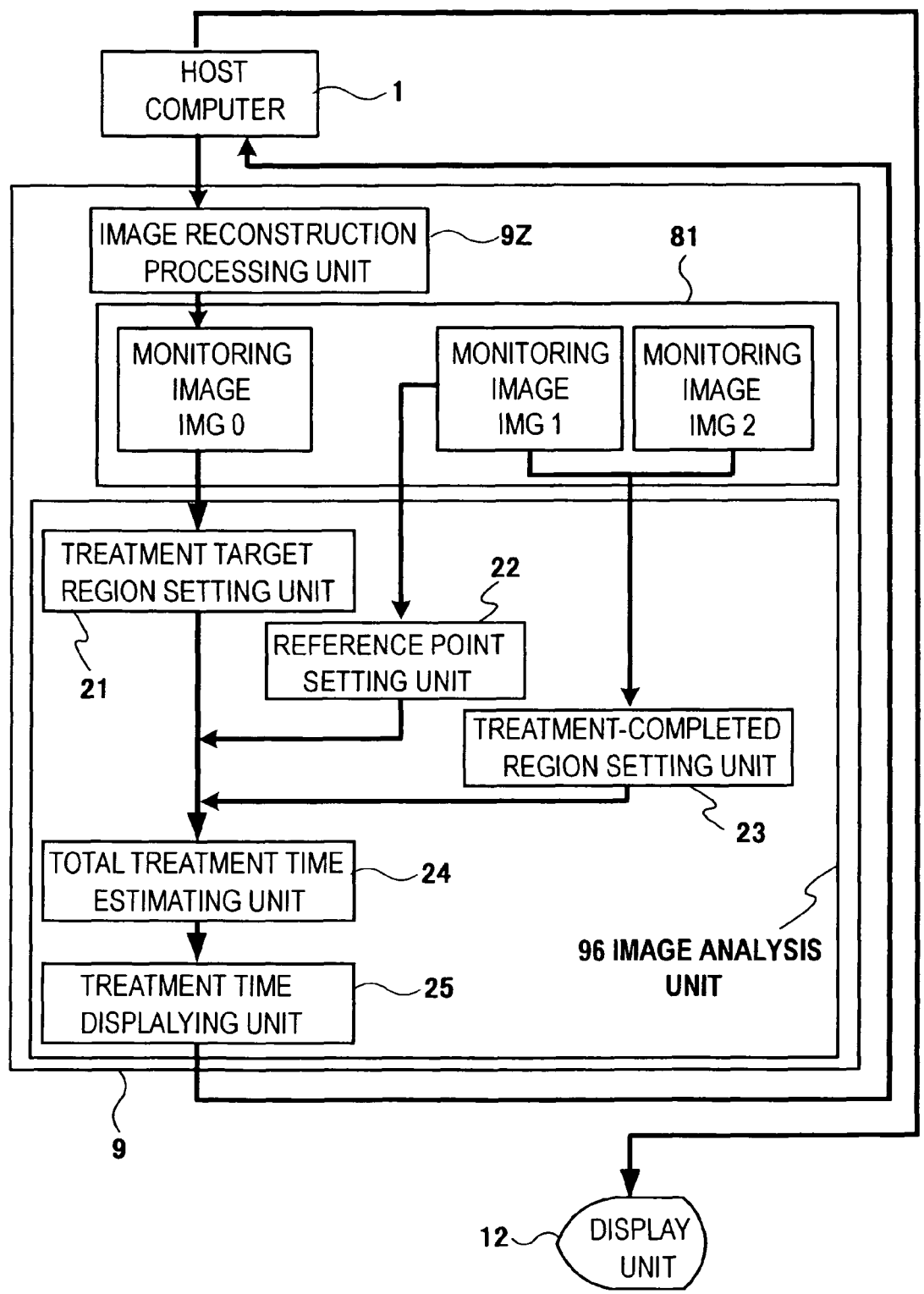
FIG. 2 is a diagram showing a configuration of an image processor relating to the embodiment of the image processor for medical treatment support by the present invention.

FIG. 2 is a diagram showing a configuration of an image processor relating to an embodiment of an image processor for medical treatment support of the present invention. This image processor comprises treatment target region setting unit 21, reference-point setting unit 22, treatment-completed region setting unit 23, total treatment-time estimating unit 24 and treatment-time indicating means 25. Treatment target region-setting unit 21 is for specifying the region that can cover the lesion thoroughly on the monitoring cross-section upon treatment, and the region can be specified with a variety of forms such as circular form, rectangle or free curve. Like in the case of cryosurgery of which the elliptical treatment region (ice ball) grows, different forms can be selected as the situation demands. Reference point setting unit 22 is generally for specifying the starting point of the treatment, and in the case of cryosurgery the reference point is set at the lowest temperature area, which is for instance, the tip of a probe. Treatment-completed region setting unit 23 is for setting the region considered to be where the temperature reached a point of which the tissues are already necrotized. The setting can be manually designated by an operator on a screen or automatically extracted by means such as threshold processing. Total treatment time estimating unit 24 is for calculating the time required to implement the treatment on the region set by treatment target region-setting unit 23. Treatment time indicating unit 25 is for displaying the estimated time of completing the treatment being calculated in total treatment time estimating unit 24 to a device such as display device 12 and indicating it to an observer.

Figure 3:
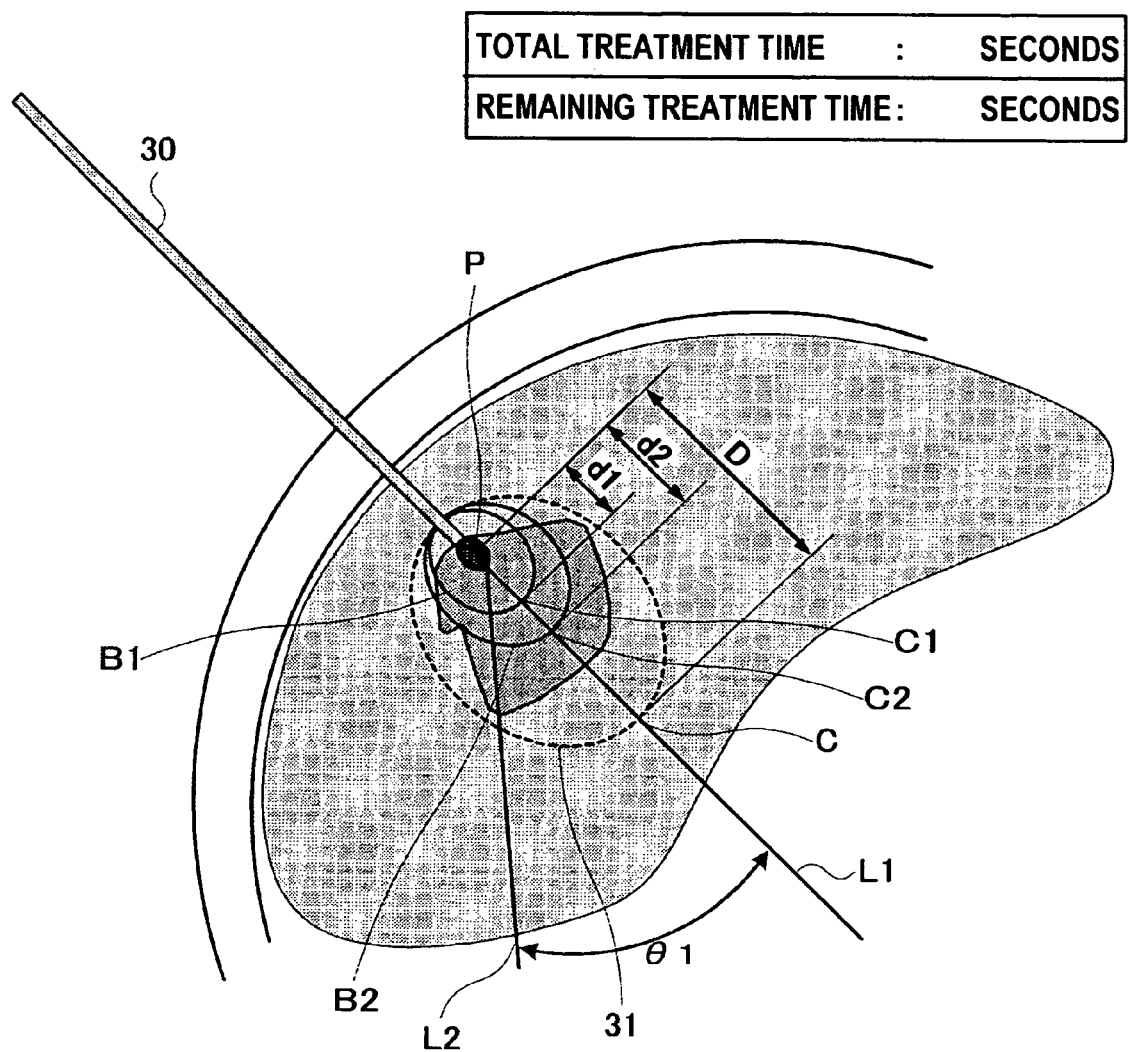
FIG. 3 is an example of a treatment support display upon a cryosurgery of a liver.
Figure 4:
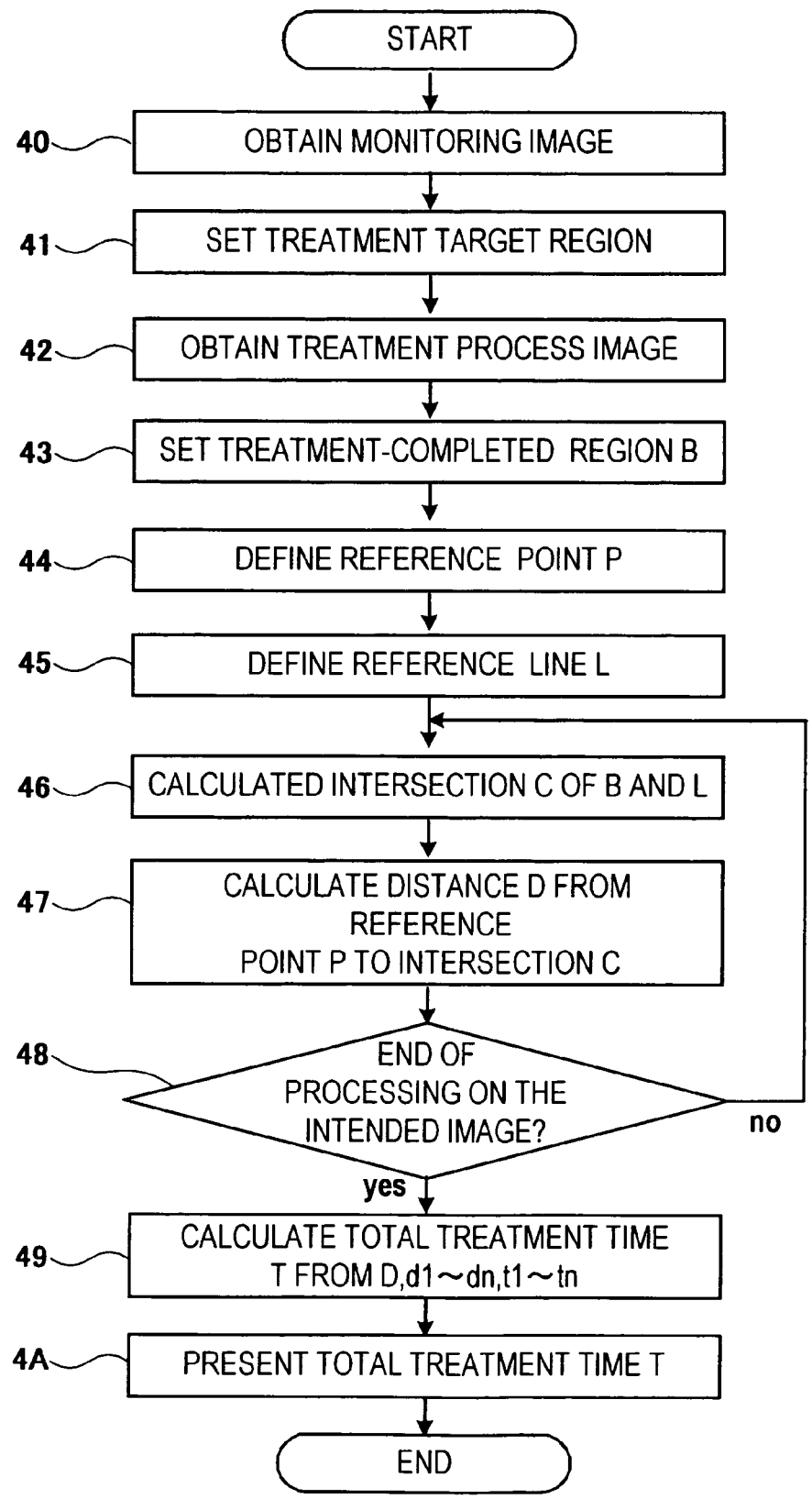
FIG. 4 is a flow chart showing the operation of the image processor for medical treatment support.

FIG. 3 is a display image of a liver upon cryosurgery displayed on the display unit. In FIG. 3, positional relation of treatment target region 31 denoted with a dotted line, treatment-completed region B1 at the time of t1, treatment-completed region B2 at the time of t2, reference point P that indicates the starting point of the treatment, and reference lines L1 and L2 for estimating the time of completing the treatment are illustrated. More specifically, a picture of the gas eradiated from the tip of probe 30 freezing the tissues sequentially from reference point P which is a vicinity of the radiation aperture, and covering the lesion portion gradually is illustrated in FIG. 3. FIG. 4 is a flow chart showing the operation of this image processor for medical treatment support. Hereinafter the operation of this image processor for medical treatment support will be described.

In step S40, the image processor for medical treatment support of the present embodiment determines a cross section for monitoring which is to be punctured prior to a treatment, and obtains it as a monitoring image IMG0.

In step S41, treatment target region setting unit 21 sets treatment target region 31 on monitoring image IMG0 using GUI (Graphical User Interface).

In step S42, a treatment is started, and the images of the treatment procedure are properly obtained for the purpose of observing them. Monitoring image IMG1 as a treatment procedure image after passing of time t1 since the starting of the treatment, and monitoring image IMG2 after passing of time t2 are respectively obtained.

In step S43, since the region frozen by the treatment is projected from the treatment process images, for example, as black low signals in MRI, treatment-completed region setting unit 23 extracts the frozen region from monitoring images IMG1 and IMG2, and sets coordinate of border thereof as treatment-completed regions B1 and B2 in respective monitoring images IMG1 and IMG2.

In step S44, reference point P is defined by reference point setting unit 22 based on monitoring image IMG1.

The processes of step S45~S49 are executed by total treatment time estimating unit 24.

In step S45, straight line L1 (a reference line for calculating the treatment region) used for estimating the time, is defined from reference point P toward the direction where the treatment region is expanding. Reference line L1 to be defined first is reference line L1 as shown in FIG. 3 being along with the eradiation direction of gas. Defining a plurality of reference lines can improve the accuracy of estimating time, even though one reference line will do. Thus in the case of defining a plurality of reference lines, angle θ from reference line L1 can be set as a parameter, or the individual coordinate being defined by the border can be used. In FIG. 3, reference line L2 is defined corresponding to reference line L1 with angle θ1.

In step S46, intersection points C1 and C2 of reference line L1 being defined from reference point P and the respective monitoring images IMG1 and IMG2 are obtained.

In step S47, distance d1 and d2 from reference point P to the respective intersection points C1 and C2 are obtained.

In step S48, determination is conducted on whether the process of steps S46 and S47 are completed on at least 2 of the monitoring images IMG1 and IMG2 that are the intended images. When it is determined that the process is completed step S49 is carried out, and when not completed the process should return to step S46, and the same procedure is to be repeated.

Figure 5:
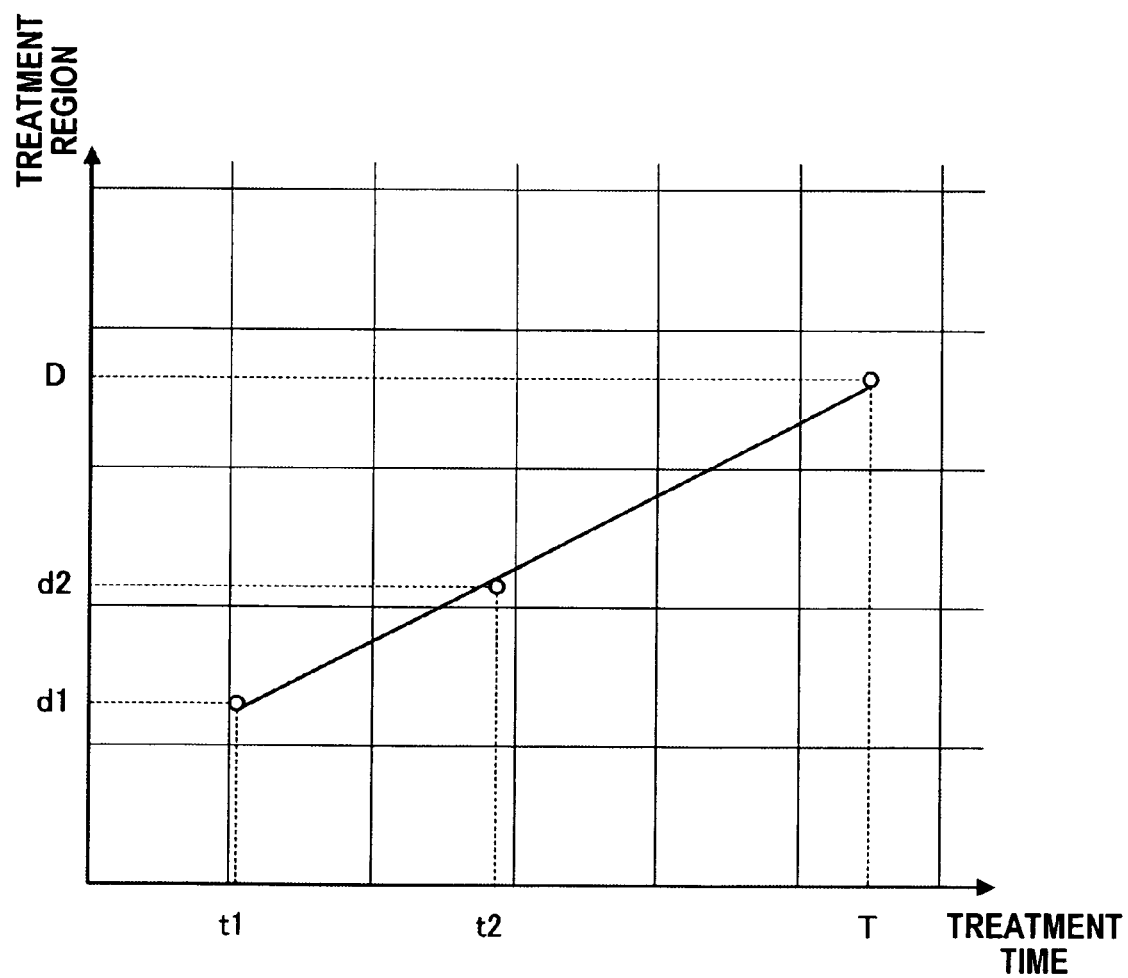
FIG. 5 is a chart showing the relation between the treatment time at monitoring an image and the distance indicating the treatment region.

In step S49, since it is already known that treatment time t1 and time t2 were required for reaching respective treatment-completed regions B1 and B2 which are the frozen regions of monitoring images IMG1 and IMG2 for indicating the treatment procedure, distance D from reference point P to intersection point C which is an intersection of treatment target region 31 being set in advance and reference line L1 is obtained, and time T which is the time required for the treatment is calculated from the relation between times t1 and t2 which are the time required to reach to distance d1 and d2 which are the distance from reference point P to the respective intersections C1 and C2. FIG. 5 is a chart showing the relation between treatment time t1, t2 in the above-mentioned monitoring images IMG1, IMG2 and distance d1, d2 that indicate the treatment region. Time T which is the time required for the treatment of treatment target region 31 can be calculated from the ratio of the above-mentioned time and distance (or by the regression), as is apparent by FIG. 5. In the case of using a plurality of probes, the same number of reference points as the number of probes can be set, and the treatment time can be obtained by setting the reference lines on the respective reference points. For example, in the case of setting a plurality of reference lines, the longest time T out of the time being calculated on the respective reference lines can be set as a treatment time, or an average of the time being calculated on the respective reference lines can also be set as a treatment time.

In step S4A, the total treatment time being calculated by the estimation of treatment-time indicating unit 25 is displayed numerically to the observer. This treatment time indicating unit 25 may be set so that the treatment-completed region and the treatment regions after a minute and after two minutes are estimated, and the estimated treatment regions thereof can be displayed on the tomographic images by hue information in incremental steps. It may also be arranged so that the permeability can be set on the colors or gray scale to be displayed, and the shading information of the monitoring images may be superposed upon display. Hue information here means the color shade, thickness or pattern of the colors including white, black and gray. Also, in the case that it is easier to figure out the positional relation with the lesion by using the image before the treatment, the image before the treatment may be used to superpose with instead of the monitoring image.

Though the case of calculating the total treatment time based on two monitoring images IMG1 and IMG2 is mentioned in the above embodiment, it is possible to estimate the total treatment time more accurately by using plural n-pieces of monitoring images.

There are various sorts of methods for setting the reference line or closed region, and in one method the total treatment time is estimated by first obtaining the intersections from barycentric position G0 toward all directions with equal angles (15? intervals on the diagram) as seen in FIG. 6(A). The lines that connect the intersection points and the reference point is set as the reference lines, and the treatment time will be estimated based on the treatment progress on these reference lines.

Alternatively the intersection points can be obtained by setting the perpendicular lines to reference line L1 at regular (irregular is also accepted) intervals as seen in FIG. 6(B). In this method, at least one reference line L1 which bisects the treatment target region from the reference point is designated, the intersection points of the treatment target region and the perpendicular lines to divide the reference line in equal (or unequal) intervals are obtained, the lines that connect those points and the reference point are further set as reference lines, and the total treatment time is estimated based on the treatment progress on these reference lines.

Or, the total treatment time can be estimated by first setting the reference lines which connect the reference point and the pixels at predetermined intervals out of the pixels on the display unit for displaying the outline of the treatment target region, and estimate the time based on the treatment progress of those reference lines. In other words, this method is for estimating the total treatment time by using the reference lines being obtained by equally sampling the number of pixels on the border pixels of the closed curve and further drawing the additional reference lines toward these sample points. In this way, the reference lines can be drawn plurally by connecting the obtained intersections and reference point P, the treatment region after passing of predetermined time can be estimated as mentioned above, and the estimated treatment region can be projected with high accuracy.

Figure 7:
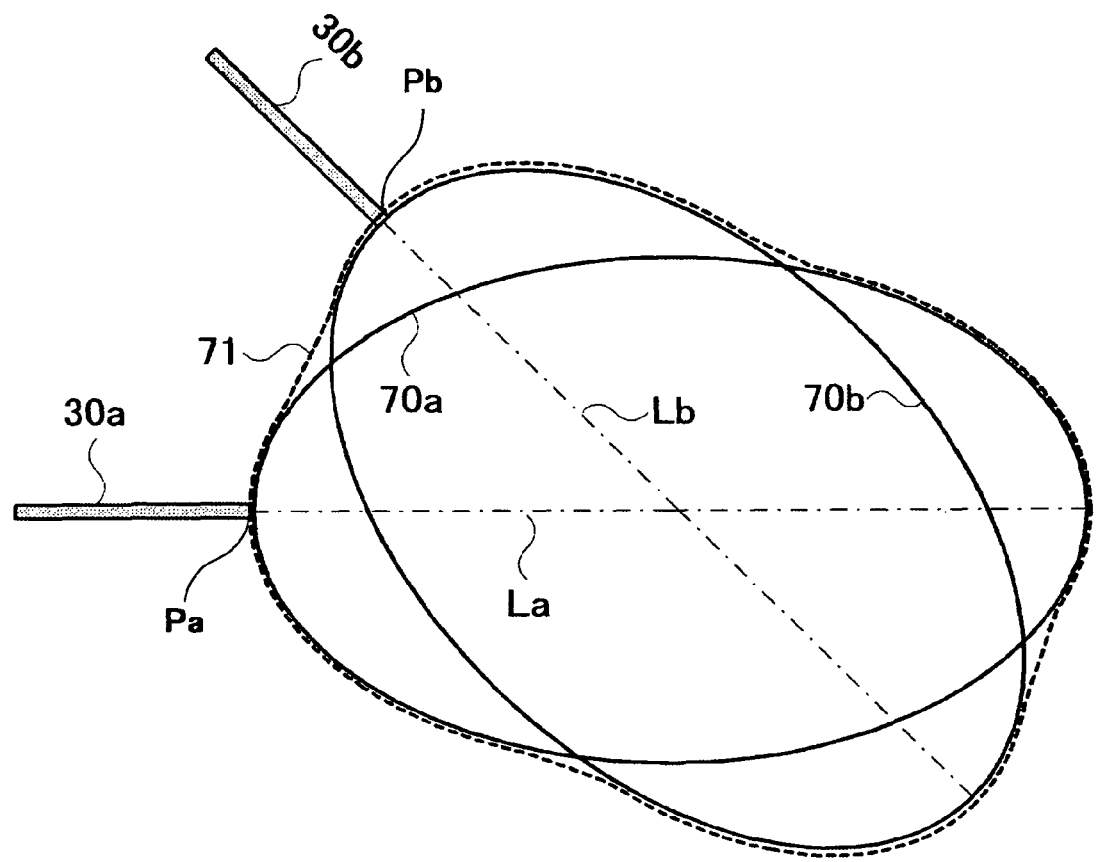
FIG. 7 is a diagram showing a setting means of a closed region in the case of using a plurality of probes.

FIG. 7 is a schematic diagram showing a method for setting a closed region in the case of using a plurality of probes. As illustrated in FIG. 7, it is desirable to set the closed regions including a plurality of reference lines La, Lb and both of closed curves 70a, 70b in the case of using a plurality of probes 30a, 30b. The region that the logical addition of both closed regions 70a and 70b is implemented on is the actual treatment region, but the vicinity of the outline appears with concave regions as seen in FIG. 7. However, it is considered that the actual treatment region is further extended over these concaved regions, thus it is desirable that these concaved regions are defined as a synthetic region 71 which is a smooth closed region (illustrated with a dotted line) on which a smoothing process is implemented.

Synthetic region 71 with a smoothing process can be determined by using information such as a continuity, angle or curvature of the borderline. As for concrete examples of the smoothing process, the degree of smoothing can be determined based on a quantitative value such as an angle oriented by a normal line of both closed regions, but the most simple and efficient means is to obtain a moving average with respect to the distance from the gravity point and to adopt the result of smoothing only to the region that the distance becomes larger. Total time required for the treatment can be estimated by using an arbitrary value such as the average value, maximal value or minimum value of the treatment progress on a plurality of reference lines.

Also, the total treatment time may be estimated by obtaining the treatment-completed regions at a plurality of time points, and implementing the functional approximation on them. For example, the relation between the treatment-time and the treatment-region may be obtained by first setting the outline of treatment-completed regions B1 and B2 of FIG. 3 as function of time on the coordinate to create the approximation formula, and by substituting the predetermined time for the time variable. Here as a means for approximating, well-known means such as curve fitting can be used.

The Second Embodiment

The configuration or the process of the present embodiment is basically the same as embodiment 1, unless particularly mentioned otherwise. Also, the same reference number illustrates the same portion as in embodiment 1.

Figure 8:
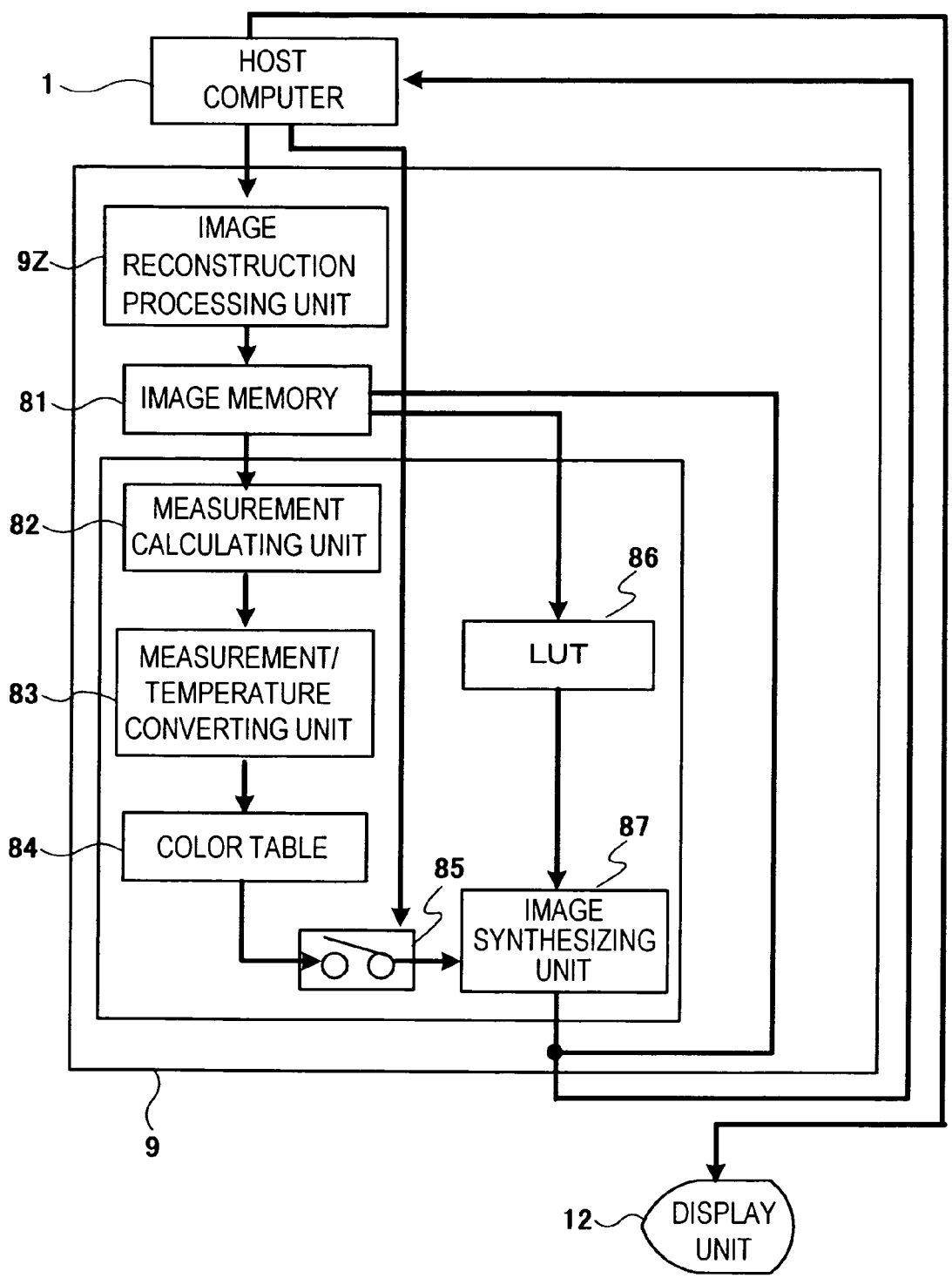
FIG. 8 is a diagram showing a configuration of an image processor relating to another embodiment of the image processor for medical treatment support of the present invention.

FIG. 8 is a diagram showing the configuration of an image processor relating to another embodiment of the image processor for medical treatment support in the present invention. This image processing unit 9 comprises measurement calculation unit 82, measurement/temperature converting unit 83, color table 84, inputting switch 85, look-up table (LUT) 86, image synthesizing unit 87, and image memory 81 as shown in FIG. 8. Image memory 81 is for storing temporarily the measurement data and measurement value being outputted from measurement circuit 5 or the tomographic image being obtained by reconstructing them. Look-up table (LUT) 86 is consistently storing a look-up table for giving a gray scale for the purpose of displaying CT images, and is set up so that, for example, the CT value of −10~90 is to be allocated to the gray scale of 0~255 when the center of display gradation is 40 in CT value and 100 in width. For example, the pixel at CT value 40 becomes 127 level of gradation value, and all of RGB values become equal. Look-up table (LUT) 86 may be set so that the measurement value is calculated from the measurement data or the tomographic image, and allocated to gray scale as mentioned above.

Figure 9:
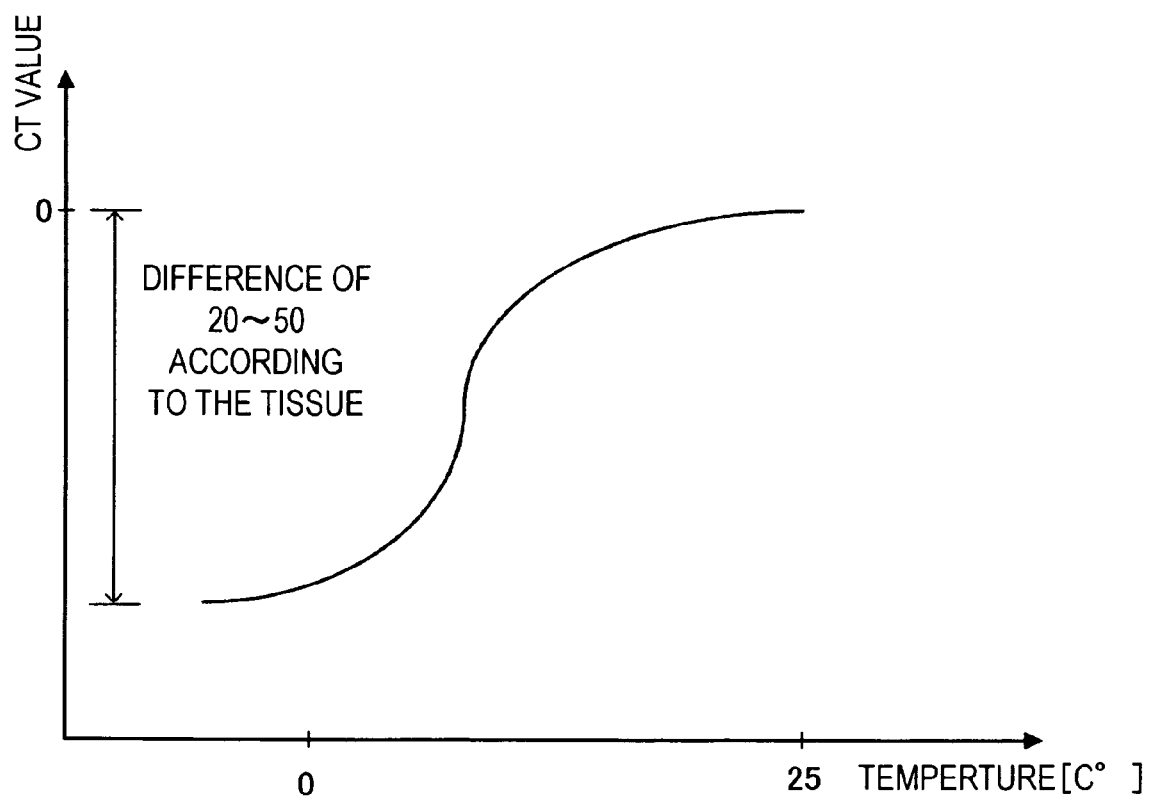
FIG. 9 is a diagram showing an example of a measurement/temperature converting means in FIG. 8.

Measurement calculating means 82 is for calculating CT value based on the measurement data from image memory 81. Measurement/temperature converting means 83 as CT value/temperature converting table as seen in FIG. 9, and is for converting CT value being outputted from measurement calculating means 82 into the temperature of the target portion. To obtain the CT value/temperature converting table, it is assumed that the most reliable means is through animal experiments conducted in advance and performed as a treatment simulation for measuring the temperature during the treatment. As an alternative method, taking images of water temperature changes can be used instead. In any case, the corresponding curve is obtained with temperature as the horizontal axis and CT value as the vertical axis as shown in FIG. 9, and put into tabular form. Color table 84 is for allocating the hue information such as color tone, cardinality, and transparency to temperature. It comprises a color table with a setting in which, for example, the color gets closer to red as the temperature rises and gets closer to blue as the temperature drops, and is for outputting color information after conversion to image synthesizing means 87 via monitoring mode switch 85.

In the case of an X-ray CT device, the reconstructed images are created based on the absolute value called "CT value", and are high in reproducibility and quantifiable. It is assumed that there is actually a variance of around 20~50 in the CT value from a frozen state to a room temperature state during cryosurgery. Monitoring mode switch 85 is for switching the monitoring mode. In FIG. 8 is an example of image-synthesizing unit 87 wherein monitoring mode switch 85 is controlled by an on/off switch. When monitoring mode switch is off the images on the display unit or on the image memory are displayed as usual by LUT 86 with a designated gradation, and when it is on the images are displayed being synthesized with the hue information being properly determined based on information such as temperature.

An operation example of the image processor in FIG. 8 will now be described. First, monitoring mode switch 85 turns on when the monitoring mode is selected during treatment. Then when region of interest of the image being stored in image memory 81 is set by inputting device 13, the CT value of the respective pixels of the region is read out by measurement calculating unit 82, and outputted to CT value/temperature converting unit 83. CT value/temperature converting unit 83 is for converting the inputted CT value into temperature information and outputting to color table 84. In cases where much noise exists, there are occasions that the temperature information is calculated as average temperature among the pixels in the vicinity by implementing the filtering process in the cross-section or toward the slice direction if a plurality of slices is being obtained.

Upon performing cryosurgery, it is preferable to execute the setting so that it displays in blue before the treatment, with the color changing to red when it is expected the temperature reaches the point of curative effect is expected, or to approach consecutively. Such color setting can be alternated without limitation to the above-mentioned example, but it is desirable that the operator can easily visibly identify when the temperature reaches the point that a curative effect can be expected in the course of treatment.

Image synthesizing unit 87 is for synthesizing the color information being converted in color table 84 based on temperature and the display color of the original CT image, and displaying it to display device 12. For example, using permeability parameter q, weighted sum of the respective RGB values is displayed as a new color. For example, when the original gradation is set as Cgray and the color corresponding with the temperature is set as Cred, Cblue and Cgreen, the new display color R,G, and B would be:

$$R=(1.0-q) \times Cred + q \times Cgray$$

$$G=(1.0-q) \times Cgreen + q \times Cgray$$

$$B=(1.0-q) \times Cblue + q \times Cgray.$$

The present invention is not limited to synthetic method of colors as mentioned above. Also, it is desirable that not only the cross-sections of axial, but also a point of view such as sagittal and coronal are displayed at the same time on the display unit. Cone beam CT that has a wide X-ray beam width is especially suitable for grasping the growth state of an ice ball in one-time imaging.

Additionally, a means for comparing the time-series images and evaluating the growth rate of the ice ball, and a function for estimating the time required for the ice ball to cover the lesion portion sufficiently may further be added.

Also, the evaluating means of the growth rate at the moment can be defined by the relationship between distance from the center of gas irradiation to the edge of the treatment region and time. An example of preferred display means is to change the color or permeability in phase from the current treatment region to the treatment region after a minute and then to after two minutes. In the display unit, the color being used is a synthesized one of originally set color and the colors of the image before or during the treatment, the image may include the reformatted image (MPR).

Embodiment 3

The above-mentioned embodiment 1 was about estimating and displaying the time up to the completion of the treatment. Instead of or additional to the time display, the images of treatment progress may be created and displayed. By this function, for example, the time or condition being required for the ice ball to cover the lesion portion sufficiently can be identified sequentially and instantly.

Embodiment 3 will now be described referring to FIG. 10 and FIG. 11. The configuration or the process of the present embodiment is basically the same as embodiment 1 unless mentioned otherwise. Also, the same reference number illustrates the same portion as in embodiment 1.

The above-mentioned display of the treatment progress image can be implemented, for example, by effecting a change on the function of total treatment-time estimating unit 94 being described in embodiment 1 to estimate the degree of progress by the minute, and by superimposing those images of completing the treatment at a plural time points onto the original tomographic image.

Figure 11:
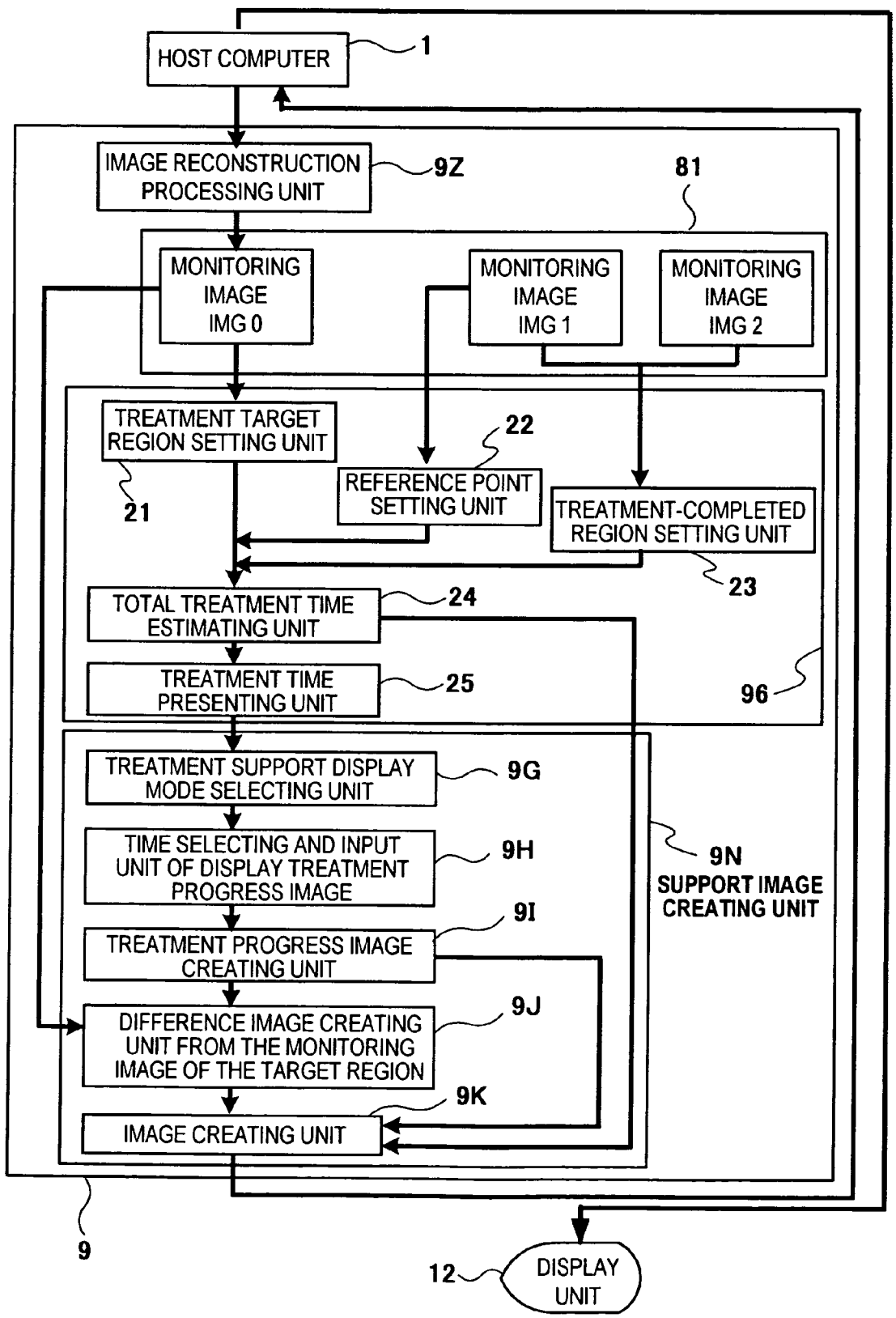
FIG. 11 is a diagram showing a configuration of an image-processing unit of the image processor for medical treatment support of FIG. 10.

As illustrated in FIG. 11, image processing unit 9 in the present invention includes support-image creating unit 9N in addition to image reconstruction processing unit 9Z, image memory 81, and image analyzing unit 96 being the same as described in embodiment 1. Support image creating unit 9N includes treatment support mode selecting unit 9G, time selecting and input means 9H for selecting and inputting the time of display treatment progress image, treatment progress image creating unit 9I, difference-image creating unit 9J for creating the difference image of the current image and the lesion monitoring image, and image creating unit 9K.

Figure 6:
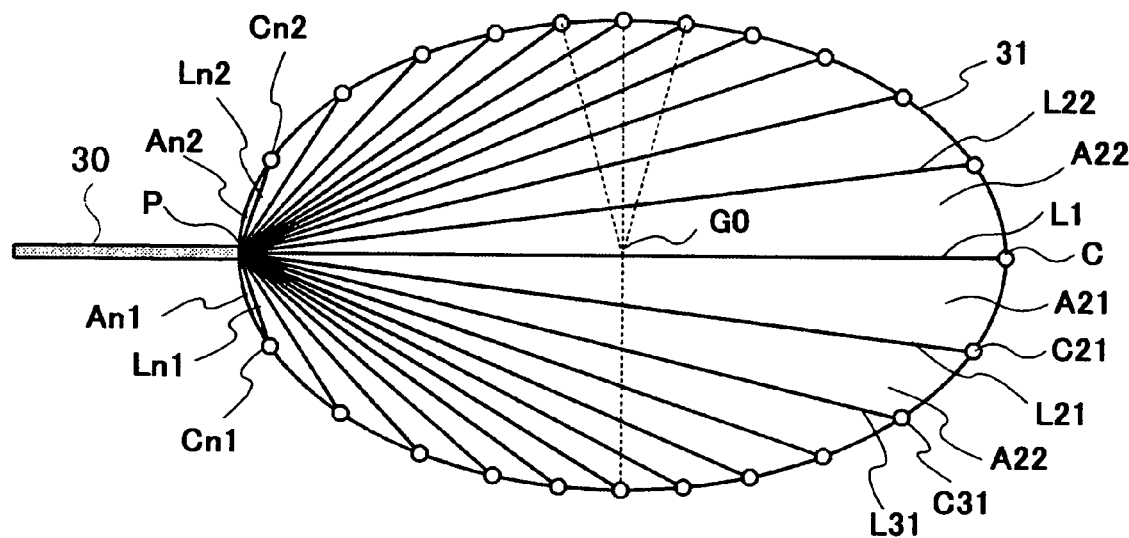
FIG. 6 is a diagram showing another example of a setting means of the reference lines or a closed region.
Figure 6:
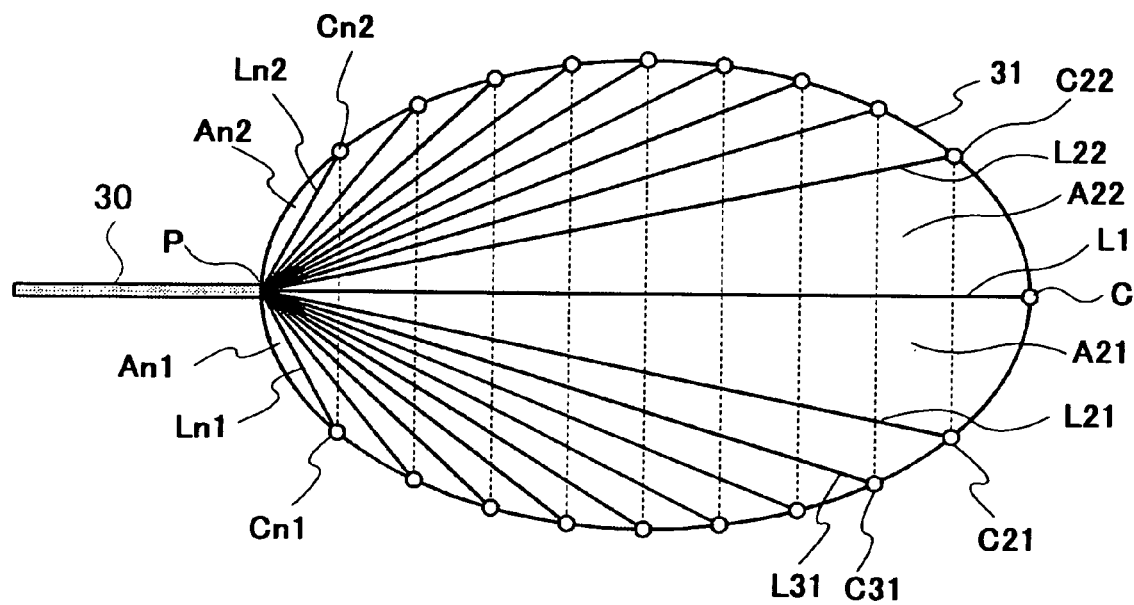
Figure 10:
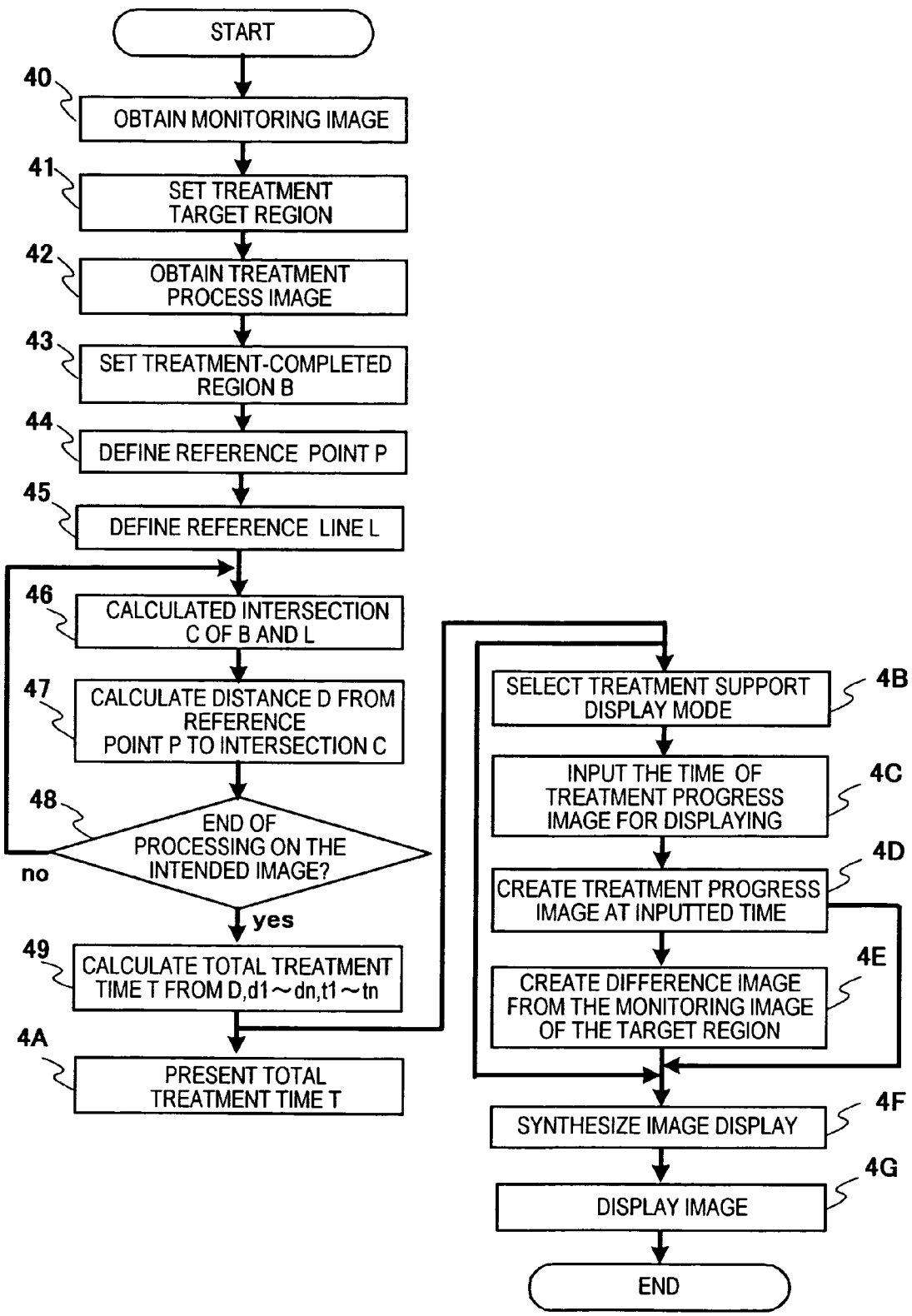
FIG. 10 is a flow chart showing the operation of the image processor for medical treatment support relating to embodiment 3.

In step 40~step 49 of FIG. 10, according to the setting of, for example, treatment target region 31 as shown in FIG. 3, the degree of treatment progress is calculated from the relationship between distances d1 and d2 which are the distances from the reference point of treatment-completed regions B1 and B2 to the respective intersections C1 and C2 and treatment times t1 and t2 which are the times required for treatment-completed regions B1 and B2 to freeze up. The steps up to this point are the same as embodiment 1, and reference line L2 may be used at the same time as described in embodiment 1, many more reference lines may be used as shown in FIG. 6, or a plurality of probes may be used as shown in FIG. 7. Even in these cases, with regard to the reference lines of the respective cases, it is possible to calculate the degree of progress on the reference line which takes the shortest time to complete the treatment, the degree of progress on the reference line which takes the longest time to complete the treatment, and the average degree of progress of all the reference lines. The time being calculated based on this information will be used as a total treatment time.

In step 4B of FIG. 11, treatment support display mode selecting unit 9G selects the mode for the treatment support display. The mode selectable for the treatment support display is total treatment time T being the same as in embodiment 1, the treatment progress image in a discretionally specified time which will be described later, the difference image between the treatment progress image in a discretionally specified time and the treatment target region or the difference image between the treatment progress image in a discretional specified time and the treatment-completed region, a chart to be described later, the treatment error image, or discretional combination of these modes.

In the case of selecting the treatment progress image in a specified time or one of the above-mentioned difference images using the treatment progress image in a specified time, the time of the treatment progress image for display should be inputted and specified to time selecting and inputting unit 9H of display treatment progress image in FIG. 11. In this case, the desired time for obtaining the treatment progress image may be specified by presenting total treatment time T in advance in step 4A and referring to it, or total treatment time T can be set by default when nothing is specified. Also, a plurality of times may be selected and inputted.

In step 4D, the treatment progress image in the inputted time in above-mentioned step 4C is created in treatment progress image creating unit 9I of FIG. 11.

In step 4E, the difference image between the treatment progress image being created in above-mentioned step 4D and image IMG0 that is the image before the treatment is created in difference image creating unit 9J for creating the difference image between the current image and the monitoring image of the lesion portion. The image for creating the difference image here need not be limited to image IMG0 being the image before the treatment, but a previous treatment progress image may be used instead.

In step 4F, according to the mode of the treatment support display being selected in step 4B, one out of total treatment time T, the treatment progress image at a specified time, and the difference image from the treatment progress image at a specified time, or any of the combination of these image displays are synthesized. The above-mentioned synthesis is executed in image creating unit 9K of FIG. 11. The imaging can be executed by displaying the treatment image of different time periods by different colors, or by superimposing temperature distribution in a certain time at the periphery of the treatment portion using the method being described in embodiment 4 for the display. By using these methods, the treatment region of, for example, after one minute and two minutes can be displayed with different colors and degrees of permeability. Also, as well as displaying the respective treatment regions of the current, after one minute, and after two minutes with a different color, the temperature distribution of the respective treatment regions may be displayed with different degrees of permeability of each color.

The treatment progress image or temperature distribution according to time can be displayed in various manners, making full use of the width or types of the lines for plotting the color coordinate or the regions.

Such display means will be valuable for determining the most suitable treatment time for the entire treatment region and the normal surrounding tissues.

The condition of treatment progress can easily be grasped by creating the difference image between the treatment progress image in step 4E and image before the treatment IMG0. The fact that the difference images are differential components contributes to more accurate evaluation of acceleration velocity of the treatment progress. For example, possible artifact components being produced in the difference images by using probe 30 or a probe can be removed conveniently. As a result of implementing a difference calculation on data, it advantageously displays only the region where the treatment is making progress.

The difference image can also be superposed on the image of, for example, IMG0 being used for the difference calculus when the difference image was created. Alternatively, by obtaining the area or volume (when three-dimensional) of the difference and displaying the area change and the volume change by a chart corresponding to the time axis, it will be easier to grasp the development of the treatment progress.

As for creating the difference images, the threshold processing or image denoising are necessary because at times the probe staggers during the treatment. As for image denoising, a well-known method can be used wherein the areas are obtained after labeling and only the noise of specific area would be the target of denoising.

Additionally, difference image creating unit 9J of the present embodiment in the case of monitoring the treatment progress by X-ray CT apparatus, is not only for using to display the estimated treatment process but also for using to extract the region where the heat transfer is being delayed due to the presence of organs such as blood vessels, by creating the treatment error-image of the treatment progress image and the treatment-completed region image being updated and obtained, and by using the error for the extraction. Different color information may be allocated to each of the following, treatment target region, treatment-completed region, treatment progress image, and the difference image. Also, the color information for allocating can be varied according to the temperature being obtained by the above-mentioned measurement/temperature converting means.

In this case, the difference region may be extracted by acknowledging the curvature or discontinuity on the images, but without limiting to this method any method can be used as long as executed by acknowledging the difference. Indications of the presence of a blood vessel in the portion where the treatment is being delayed can be given to the physician by executing such method. The physician can evaluate the result of this and change the treatment plan if necessary, in order to avoid the blockage of the blood vessel which is not the objective of the treatment.

In addition, the image used in any of the above-mentioned embodiment may be a reformated image (MPR). Also, it is preferable that the cross-sections of not only axial but a point of view such as sagittal or coronal, or three-dimensional image are displayed at the same time.

Particularly, in case of using a cone-beam CT with a wide X-ray beam width, further improves the treatment since a three-dimensional image and the growth condition of the ice ball from the point of view such as axial, sagittal or coronal can be grasped in one-time imaging.

INDUSTRIAL APPLICABILITY

As described above, according to the present invention, by enabling to monitor during the treatment and to estimate the time required up to the completion of the treatment, the accuracy of the remaining treatment plan can be improved. Further, by reducing the number of obtained the images in order to carry on the treatment according to the plan, rapid ablation therapy can take place. Especially in the case of using X-ray images, the amount of exposure to radiation can be reduced since the imaging takes place only the minimum number of times necessary for the treatment. Also, treatment conditions such as positioning of a lesion and a treatment target region, presence of the blood vessel in a target treatment region, or temperature can easily be understood at the time of monitoring during treatment, thus remarkably valuable support information for the treatment can be provided.

The invention claimed is:

1. An image processor for medical treatment support for monitoring the treatment process by obtaining a tomographic image of an object to be examined comprising:
    a treatment target region setting means for selecting a monitoring image from the tomographic image, and for setting a treatment region as an objective on the image thereof;
    a treatment-completed region setting means for setting the region where the treatment is already considered completed on the monitoring image; and
    a total treatment time estimating means for estimating the time up to the completion of the treatment target region being set by the treatment target region setting means based on the treatment-completed region,
    wherein the total treatment time estimating means obtains each of the distance from a reference point which is the starting point of the treatment to the outline of the treatment-completed region with regard to the treatment-completed region on a plurality of monitoring images, and estimates the total treatment time based on the change of distance.

2. The image processor for medical treatment support according to claim 1, wherein the total treatment time estimating means, on the treatment target region, sets straight lines being extended radially from the reference point at equiangular intervals as the reference lines, and estimates the total treatment time based on the treatment progress on the reference lines.

3. The image processor for medical treatment support according to claim 2,
    wherein the treatment target region setting means sets the region by synthesizing a plurality of closed curves and smoothing the cross-over sections thereof, and
    the total treatment time estimating means sets reference lines on every said closed curve, and estimates the total treatment time based on the treatment progress of those plurality of reference lines.

4. The image processor for medical treatment support according to claim 1, wherein the total treatment time estimating means specifies at least one reference line which bisects the treatment target region from the reference point, obtains the points of which perpendicular lines to divide the reference lines with predetermined intervals intersect with the treatment target region, sets the lines connecting these points and the reference point as further reference lines, and estimates the total treatment time based on the treatment progress on the further reference lines.

5. The image processor for medical treatment support according to claim 1, wherein the total treatment time estimating means sets the lines connecting the reference point and the pixels with predetermined intervals out of the pixels on a display means for displaying the outline of the treatment target region as the reference lines, and estimates the total treatment time based on the treatment progress on the reference lines.

6. The image processor for medical treatment support for obtaining a tomographic image of an object to be examined and monitoring the treatment process comprising:
    a treatment target setting means for selecting the monitoring image from the tomographic image, and setting the treatment region on it as an objective;
    a treatment-completed region setting means for setting the treatment-completed region which is a region considered that the treatment is already completed on the monitoring image; and
    a display means for estimating the treatment region after passing a predetermined time based on the treatment-completed region, and displaying this estimated treatment region with at least one hue information,
    wherein the display means displays as allocating different hue information to each of the treatment target region, treatment-completed region and the estimated treatment region.

7. The image processor for medical treatment support according to claim 6, wherein the display means displays, as allocating the hue information to the above-mentioned treatment target region.

8. The image processor for medical treatment support according to claim 6, wherein the display means displays as allocating hue information to the treatment target region, as well as the change of the region under treatment with color indication.

9. The image processor for medical treatment support according to claim 6, wherein the display means displays as allocating different hue information to each of the treatment-completed regions at a plurality of time points.

10. The image processor for medical treatment support according to claim 6, wherein the display means displays as allocating hue information in incremental steps to the estimated treatment region.

11. The image processor for medical treatment support according to claim 6, wherein the display means displays each of the above- mentioned estimated treatment regions at a plurality of points with desired color gradation.

12. The image processor for medical treatment support according to claim 6, wherein the display means displays by superimposing one or both of the estimated treatment-region and/or the treatment-completed region on the treatment target region.

13. The image processor for medical treatment support according to claim 1, comprising:
- a treatment support display mode selecting means for selecting the display mode for treatment support;
- a time selecting and input means for inputting the time after the starting of treatment, of the treatment progress image being intended to display;
- a treatment progress image creating means for creating the treatment progress image at selected times; and
- a display means for displaying one or both of the treatment target means and/or treatment-completed region, and the treatment progress image.

14. The image processor for medical treatment support according to claim 13, comprising a difference image creating means for creating a difference image of one or both of the treatment target region and/or the treatment-completed region and the treatment progress image, wherein the display means displays one or both of the treatment target region and/or the treatment-completed region and the difference image.

15. The image processor for medical treatment support according to claim 13, wherein the display means displays as allocating different hue information to the treatment target image, the treatment-completed image, the treatment progress image and the difference image.

16. The image processor for medical treatment support for obtaining a tomographic image of an object to be examined, and monitoring the treatment process comprising:
- an image memory for storing data for creating the tomographic image;
- a measurement calculating means for obtaining the measurement value from the data for creating the tomographic image;
- a measurement/temperature converting means for converting the measurement value into temperature;
- a color table for temperature-color display by allocating hue information with regard to the temperature being converted;
- a look-up table for allocating the gray scale to the data for creating the tomographic image being stored in the image memory;
- a monitoring mode switch for indicating the sysnthesis of the temperature-color display and the data for creating the tomographic image being allocated with gray scale; and
- a display means for displaying the synthesized image of temperature-color display and the data for creating the tomographic image as an image,
- wherein the measurement/temperature converting means converts CT value into temperature, by setting CT value as measurement value that the tissue in the vicinity of 25 degrees of which the CT value is 0 has the CT value of −20~−50 at below 0 degree of temperature.

* * * * *